US009956538B2

(12) United States Patent
Chin et al.

(10) Patent No.: US 9,956,538 B2
(45) Date of Patent: May 1, 2018

(54) PHOTO-RESPONSIVE MACRO- AND MICRO-LIQUID MARBLES

(71) Applicant: Agency for Science, Technology and Research, Singapore (SG)

(72) Inventors: Jia Min Chin, Singapore (SG); Siok Wei Tay, Singapore (SG); Xiaobai Wang, Singapore (SG); Jianwei Xu, Singapore (SG); Andy Tzi Sum Hor, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days. days.

(21) Appl. No.: 14/764,832

(22) PCT Filed: Feb. 13, 2014

(86) PCT No.: PCT/SG2014/000056
§ 371 (c)(1),
(2) Date: Jul. 30, 2015

(87) PCT Pub. No.: WO2014/126536
PCT Pub. Date: Aug. 21, 2014

(65) Prior Publication Data
US 2015/0367316 A1 Dec. 24, 2015

(30) Foreign Application Priority Data
Feb. 15, 2015 (SG) ................. 201301172-1

(51) Int. Cl.
| *A61K 9/48*  | (2006.01) |
| *B01J 19/12* | (2006.01) |
| *A61K 41/00* | (2006.01) |
| *C05G 3/00*  | (2006.01) |
| *G21K 5/02*  | (2006.01) |
| *A61K 9/50*  | (2006.01) |
| *B82Y 5/00*  | (2011.01) |
| *B82Y 30/00* | (2011.01) |

(52) U.S. Cl.
CPC ............ *B01J 19/12* (2013.01); *A61K 9/4808* (2013.01); *A61K 41/0028* (2013.01); *C05G 3/0005* (2013.01); *C05G 3/0017* (2013.01); *C05G 3/0041* (2013.01); *C05G 3/0076* (2013.01); *G21K 5/02* (2013.01); *A61K 9/501* (2013.01); *A61K 9/5015* (2013.01); *B01J 2219/089* (2013.01); *B01J 2219/12* (2013.01); *B82Y 5/00* (2013.01); *B82Y 30/00* (2013.01)

(58) Field of Classification Search
None
See application file for complete search history.

(56) References Cited

U.S. PATENT DOCUMENTS 8,226,961 B2    7/2012  Seu-Salerno et al.
2013/0264287 A1* 10/2013 Zhang ............... C02F 1/40
                                              210/639

FOREIGN PATENT DOCUMENTS

GB       2467780 A      8/2010
WO    2007042833 A2     4/2007

OTHER PUBLICATIONS

McHale et al., "Capillary Origami: Superhydrophobic Ribbon Surfaces and Liquid Marbles," Beilstein Journal of Nanotechnology, vol. 2, 2011, pp. 145-151.
Wang et al., "Methane Storage in Dry Water Gas Hydrates," J. Am. Chem. Soc., vol. 130, 2008, pp. 11608-11609.
McEleney et al., "Liquid Marble Formation Using Hydrophobic Powders," Chem. Eng. J., vol. 147(2), 2009, pp. 373-382.
Aussillous et al, "Liquid Marbles," Nature, vol. 411, 2001, pp. 924-927.
Eshtiaghi et al., "A Quantitative Framework for the Formation of Liquid Marbles and Hollow Granules from Hydrophobic Powders," Powder Technol., vol. 223, 2012, pp. 65-76.
Y. R. Mahajan, "Nanotechnology-Based Solutions for Oil Spills," Nanotech Insights, Jan. 2011, http://www.nanowerk.com/spotlight/spotid=20215.php, pp. 1-14.
International Preliminary Report on Patentability for International Application No. PCT/SG2014/000056 dated Nov. 27, 2014, pp. 1-5.
Zhang et al., "Remotely Controllable Liquid Marbles," Advanced Materials, vol. 24, Issue 35, Sep. 11, 2012, pp. 4756-4760.
Corrected Version of International Preliminary Report on Patentability for International Application No. PCT/SG2014/000056 dated Nov. 27, 2014, pp. 1-14.

* cited by examiner

*Primary Examiner* — Jake Vu
(74) *Attorney, Agent, or Firm* — Winstead, P.C.

(57) ABSTRACT

The invention relates to macro- and micro-liquid marbles (i.e. droplets of liquid with a particulate-based shell), and in particular, to photo-responsive macro- and micro-liquid marbles encapsulating a substance therein. Methods for forming the macro- and micro-liquid marbles, and use of the macro- and micro-liquid marbles, in controlled release applications are also disclosed.

7 Claims, 6 Drawing Sheets

Pink marble        Yellow marble

Pink marble        Yellow puddle

Plurality of nanoparticles forming a shell

| Wavelength / nm | Dry Water (partial silica coating) |
|---|---|
| 300 | 15 minutes (70 wt% H$_2$O) |
| 350 | 15 minutes (86 wt% H$_2$O) <br> 25 minutes (70 wt% H$_2$O) |

PHOTO-RESPONSIVE MACRO- AND MICRO-LIQUID MARBLES

CROSS-REFERENCE TO RELATED APPLICATION

This application claims the benefit of priority of Singapore Patent Application No. 201301172-1, filed Feb. 15, 2013, the contents of which being hereby incorporated by reference in its entirety for all purposes.

TECHNICAL FIELD

The invention relates to macro- and micro-liquid marbles (i.e. droplets of liquid with a particulate-based shell), and in particular, to photo-responsive macro- and micro-liquid marbles encapsulating a substance therein. Methods for forming the macro- and micro-liquid marbles, and use of the macro- and micro-liquid marbles, in controlled release applications are also disclosed.

BACKGROUND

Metal oxide particles (nano-, submicro- and microparticles) are used in many areas including polymer and particle composites, Pickering emulsions, photocatalysis and even in sunscreens. However, the use of these particles in lipophilic materials such as polymers or in sunscreen lotions necessitates their surface treatment to yield hydrophobic particles. This allows stable dispersions and composites of these particles to be formed. As such, a simple and economical process for hydrophobicization of such metal oxide particles is extremely important.

Further, the use of physical sunscreens such as zinc oxide (ZnO) and titanium dioxide ($TiO_2$) necessitates the encapsulation of ZnO or $TiO_2$ particles with silicon dioxide ($SiO_2$) or alumina to minimize the formation of reactive oxygen species (ROS) on the particulate surfaces due to charge separation when the particles are exposed to UV irradiation. As such, the utilization of such sunscreens in the presence of free radical scavengers such as ascorbic acid would be beneficial in aiding the quenching of these ROS. Further, it would be beneficial if the scavengers are released upon UV irradiation, to wipe up free radical species as they are formed.

It is well known to persons skilled in the art that dry water essentially refers to micronized droplets of water encapsulated by hydrophobic particles. Dry water is of wide interest to the industrial community, in particular, for the use of cosmetic compositions and also as dry paints.

On a similar note, the term "dry oil" as used herein refers to micronized liquid marbles of oil-based liquids.

Controlled release of an active substance, whereby the release is typically triggered or activated upon application of or exposure to a stimulus, is desirable in many applications. For example, in the agricultural context, the stimuli-responsive release of biocides, pesticides, fungicides, herbicides, or fertilizers is extremely useful.

In other contexts, the stimuli-induced release can also be useful for self-healing materials, release of inks, or fragrances.

SUMMARY

In one aspect of the invention, there is provided a method for releasing a substance from a macro- or micro-liquid marble. The macro- or micro-liquid marble is formed by a plurality of nanoparticles (and/or mixture of plurality of nanoparticles) and said substance is encapsulated therein. Each of the plurality of the nanoparticles is hydrophobic or oleophobic or both. The method includes irradiating the plurality of nanoparticles at a wavelength of between about 200 nm and about 2,000 nm.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DESCRIPTION

Figure 1A:
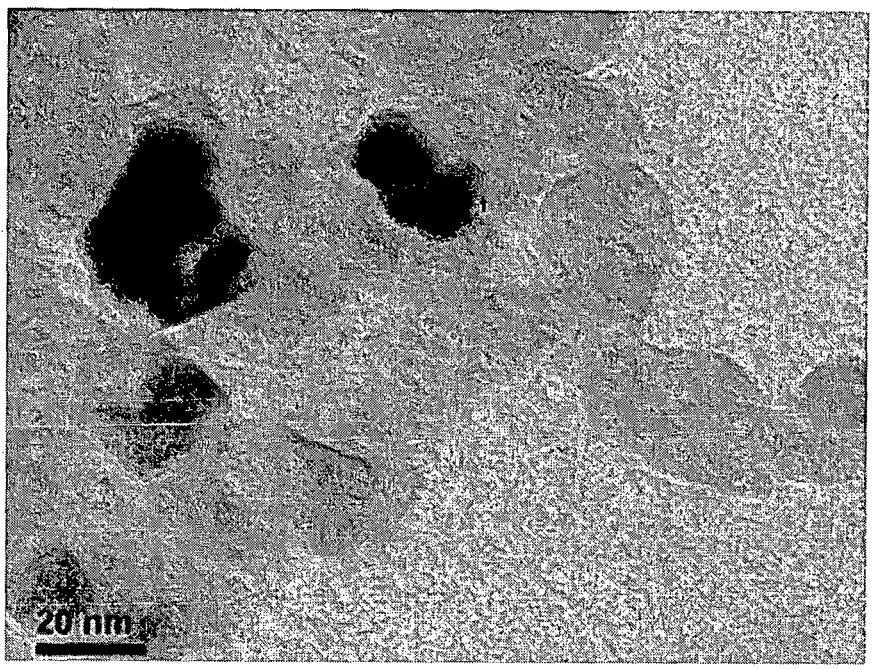
FIG. 1A shows a TEM image of 1H, 1H, 2H, 2H-perfluorooctytriethoxysilane treated $TiO_2$ particles. The small crystallites studding the larger crystals are siloxide crystallites.

The following detailed description refers to the accompanying drawings that show, by way of illustration, specific details and embodiments in which the invention may be practiced. These embodiments are described in sufficient detail to enable those skilled in the art to practise the invention. Other embodiments may be utilized and structural, logical, and chemical changes may be made without departing from the scope of the invention. The various embodiments are not necessarily mutually exclusive, as some embodiments can be combined with one or more other embodiments to form new embodiments.

Photo-responsive release of an active substance from a liquid marble, such as a macro- or micro-liquid marble, is particularly useful in an outdoor context when sunlight may induce the release of the active substance from the liquid marble. For example, photo-responsive release of chemicals or enzymes could be very useful in the cleaning up of oil-spills. The scattering of photo-responsive liquid marbles containing active substances for the breakdown of oil-spills onto a spill site would lead to the release of the active substances, such as titanium dioxide ($TiO_2$), upon photo-activation. Further, the photo-activated $TiO_2$ is still mostly hydrophobic, which would induce its association with oil, and can help to catalyse oil break-down as well.

In another example, the photo-responsive liquid marbles can be used in photoactive sunscreens, where release of antioxidants from "dry water" could be actuated by UV irradiation. In addition, slow release of moisture/oils to the skin from exposure to sunlight could be achieved, inducing a cooling or soothing effect, which is particularly attractive to cosmetics companies. For example, active cosmetic ingredients may include antioxidants, vitamins, retinoids, alpha hydroxy acids (AHAs), enzymes, phytochemicals, essential oils, or a mixture thereof. Subsequently, through homogenizing or rapid mixing of the nanoparticles with water-based mixtures, "dry water" may be formed with water comprising approximately 10-99% by weight. This dry water may exist as an aqueous solution of actives such as ascorbic acid, vitamin B, various antioxidants, salicylic acid, pigments, and dyes. Finally, the photo-stimulated release of encapsulated water/aqueous solution can be induced by irradiation with UV light.

Other exemplary applications of such photo-responsive liquid marbles may include agricultural applications where fertilizers, pesticides, and herbicides may be released upon photo-activation, or in therapeutic or self-healing applications where pharmaceutical active ingredients may be released upon photo-activation.

Disclosed herein are the preparation methods of hydrophobic and/or oleophobic nanoparticles (such as $TiO_2$ and ZnO) and their uses thereof. It includes, but is not limited to, the photo-responsive wettability changes of the nanoparticles to impart stimuli-responsiveness and the uses of this photo-response as a result.

According to one aspect of the invention, a method for releasing a substance from a macro- or micro-liquid marble is disclosed. The macro- or micro-liquid marble is formed by a plurality of nanoparticles and said substance (as part of or the entirety of a liquid or gel) is encapsulated therein. Each of the plurality of the nanoparticles is hydrophobic or oleophobic or amphiphobic (i.e. both hydrophobic and oleophobic). The method includes irradiating the plurality of nanoparticles at a wavelength of between about 200 nm and about 2,000 nm. The plurality of nanoparticles may be comprised of the same or different type. In other words, a mixture of plurality of nanoparticles may be used to form the macro- or micro-liquid marble.

As mentioned above, depending on the type of application or intended use of the substance encapsulated in the macro- or micro-liquid marble, the substance may be chosen accordingly. Correspondingly, each of the plurality of nanoparticles may be hydrophobic or oleophobic or amphiphobic, depending on the substance to be encapsulated.

In various embodiments, the substance encapsulated by the plurality of nanoparticles may be in a liquid phase, although not necessarily to be so. For example, the substance may include water or an aqueous solution. Alternatively, the substance may include oil or an organic liquid.

In various embodiments, the substance may further include a pharmaceutical active ingredient, an anti-oxidant, a dispersant, a fertilizer, a pesticide, a herbicide, or a mixture thereof.

Figures 7, 8:
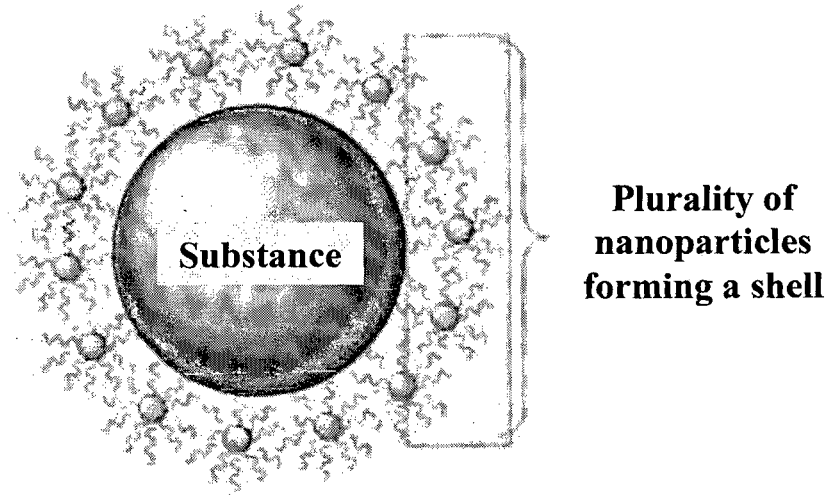
FIG. 7 shows a schematic drawing of "dry water" or "dry oil" formed by a plurality of organo- or polymer modified-nanoparticles (i.e. a shell) encapsulating the substance.
FIG. 8 shows that the "dry liquid" has different release times under UV irradiation using a Rayonet Photoreactor Chamber.

FIG. 7 shows a schematic drawing of "dry water" or "dry oil" formed by a plurality of organo- or polymer modified-nanoparticles (i.e. a shell) encapsulating the substance. The plurality of nanoparticles surrounds the substance and thus forms a shell, entrapping the substance therein. The entire structure of the shell formed by the plurality of nanoparticles surrounding the substance is herein termed as a macro- or micro-liquid marble, depending on the size of the resulting structure formed.

The encapsulated substance may be released from the macro- or micro-liquid marble by rupturing the shell formed by the plurality of nanoparticles. The rupturing may be a complete breakdown or a partial breakdown of the shell structure, so long as the macro- or micro-liquid marble becomes unstable and allows the entrapped substance to be released therefrom. The rupture is achieved by irradiating the plurality of nanoparticles, which are photo-responsive, at a wavelength of between about 200 nm and about 2,000 nm. For example, the wavelength of the radiation may be 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1,000 nm, 1,050 nm, 1,100 nm, 1,150 nm, 1,200 nm, 1,250 nm, 1,300 nm, 1,350 nm, 1,400 nm, 1,450 nm, 1,500 nm, 1,550 nm, 1,600 nm, 1,650 nm, 1,700 nm, 1,750 nm, 1,800 nm, 1,850 nm, 1,900 nm, 1,950 nm, or 2,000 nm. In further examples, the method may include irradiating the plurality of nanoparticles at a wavelength of between about 200 nm and about 2,000 nm with an intensity of more than 0.01 $mW/cm^2$.

In various embodiments, the plurality of nanoparticles may include a material selected from the group consisting of a metal, a metal oxide, an organic compound, a polymer, and a mixture thereof. In certain embodiments, one or more of the plurality of nanoparticles are surface-treated to afford the desirable surface energies.

For example, the plurality of nanoparticles may include titanium dioxide ($TiO_2$), zinc oxide (ZnO), or cerium oxide ($CeO_2$).

In another example, the plurality of nanoparticles may include a hydrophobic and/or an oleophobic polymer.

If the encapsulated substance includes water or an aqueous solution, then hydrophobic nanoparticles are chosen to form the shell entrapping the substance, thereby obtaining a dry water.

If the encapsulated substance includes oil or an organic liquid, then oleophobic nanoparticles are chosen to form the shell entrapping the substance, thereby forming a dry oil.

Various methods for forming the hydrophobic and/or oleophobic nanoparticles are disclosed herein. In various embodiments where the plurality of nanoparticles is metal or metal oxide nanoparticles, the plurality of nanoparticles may be grafted with hydrophobic and/or oleophobic groups or molecules. The hydrophobic and/or oleophobic groups or molecules may be selected from the group consisting of a silane, a silicone-based polymer, a fatty acid or a derivative thereof, an alkyl amine, and a mixture thereof.

For example, in the case of hydrophobicization of $TiO_2$, ZnO and $CeO_2$ nanoparticles, the nanoparticles may be reacted with a carboxylic acid, RCOOH, where R is a hydrophobic group such as fluorinated or non-fluorinated hydrocarbon chain. The nanoparticles may also be hydrophobicized through silanization with a silane reagent containing an alkyl, a fluoroalkyl or any other hydrophobic group.

The term "alkyl", alone or in combination, refers to a fully saturated aliphatic hydrocarbon. In certain embodiments, alkyls are optionally substituted. In certain embodiments, an alkyl comprises 1 to 18 carbon atoms, for example 6 to 18 carbon atoms, wherein (whenever it appears herein in any of the definitions given below) a numerical range, such as "1 to 18" or "$C_1$-$C_{18}$", refers to each integer in the given range, e.g. "$C_1$-$C_{18}$ alkyl" means that an alkyl group comprising only 1 carbon atom, 2 carbon atoms, 3 carbon atoms, etc., up to and including 18 carbon atoms. Examples of alkyl groups include, but are not limited to, methyl, ethyl, n-propyl, isopropyl, n-butyl, isobutyl, sec-butyl, tert-butyl, tert-amyl, pentyl, hexyl, heptyl, octyl and the like.

According to certain embodiments where dry water is desired, the nanoparticles may be grafted with hydrophobic molecules including a silane of formula $RSi(OR')_3$. R is a $C_6$-$C_{18}$ alkyl and R' is a $C_1$-$C_3$ alkyl. For example, R in $RSi(OR')_3$ may be dodecyl, hexadecyl, or octadecyl and R' in $RSi(OR')_3$ may be methyl, ethyl, propyl.

In alternative embodiments where dry water, is desired, the nanoparticles may be grafted with hydrophobic molecules including a silane of formula $RSiX_3$, $R_2SiX_2$, or $R_3SiX$. R is a $C_1$-$C_{18}$ alkyl and X is a halogen. For example, R in $RSiX_3$, $R_2SiX_2$, or $R_3SiX$ may be methyl, dodecyl, hexadecyl, or octadecyl.

According to certain embodiments where dry oil is desired, the nanoparticles may be grafted with oleophobic molecules including a fluorinated or a perfluorinated silane of formula $RSi(OR')_3$ or $RSiX_3$. R is a fluorinated or a perfluorinated $C_6$-$C_{18}$ alkyl and X is a halogen. For example, R in $RSi(OR')_3$ may be $CF_3(CF_2)_5CH_2CH_2$— or $CF_3(CF_2)_7CH_2CH_2$—.

According to other embodiments where dry oil is desired, the nanoparticles may be grafted with oleophobic molecules including a fluorinated or a perfluorinated fatty acid of formula RCOOH. R is a fluorinated or a perfluorinated $C_6$-$C_{18}$ alkyl. For example, R in RCOOH may be $CF_3(CF_2)_5CH_2CH_2$— or $CF_3(CF_2)_7CH_2CH_2$—.

In yet further embodiments where dry oil is desired, the nanoparticles may be grafted with oleophobic molecules including a fluorinated or a perfluorinated fatty acid chloride of formula RCOCl. R is a fluorinated or a perfluorinated $C_6$-$C_{18}$ alkyl. For example, R in RCOCl may be $CF_3(CF_2)_5CH_2CH_2$— or $CF_3(CF_2)_7CH_2CH_2$—.

In further other embodiments, the plurality of nanoparticles may include an organic compound such as an azo-containing compound, a stilbene-containing compound, or a mixture thereof.

In summary, it is herein described the use of photo-responsive, hydrophobic and/or oleophobic nanoparticles encapsulating a substance for controlled release. By utilizing the photo-responsive wettability of metal oxides such as $TiO_2$ and/or ZnO, photo-stimulated release of dry water or dry oil contents can be achieved. The photo-response arises from utilizing the nanoparticles which demonstrate UV-response, forming holes and electrons which migrate to the surface of the nanoparticles. This increases the surface energy of the nanoparticles, therefore increasing their wettability. The increased wettability de-stabilizes the liquid marbles/dry water, leading to release of the contents. Since the stability of dry water or dry oil is dependent on the hydrophobicity and/or oleophobicity of the particulate shell surrounding the core substance, by changing the hydrophobicity and/or oleophobicity of the encapsulating nanoparticles, the dry water or dry oil can be ruptured, thereby releasing the substance. By using different metal oxides or doped metal oxides, the photo-response of the nanoparticles and therefore the wavelength of light that induces the release can be tuned.

In order that the invention may be readily understood and put into practical effect, particular embodiments will now be described by way of the following non-limiting examples.

EXAMPLES

Example 1: Method for Hydrophobicization of Nanoparticles Through Reaction with Oleic Acid Functionalization of $TiO_2$ nanoparticles by oleic acid may occur as follows: $TiO_2$ nanopowder (Degussa, P25, 8.01 g) was placed in an autoclavable glass bottle. Oleic acid (10.25 mL, warmed to RT) was added to the bottle. MeCN (120 mL) was added to the bottle. The mixture was sonicated for 10 minutes, and then placed in an oven for 17 hours at 80° C. The powder was centrifuged to collect, and washed twice with EtOH. Yield: 5.055 g.

Example 2: Method for Hydrophobicization of Nanoparticles Through Reaction with Stearic Acid Functionalization of $TiO_2$ nanoparticles by steric acid may occur as follows: Stearic acid (1.05 g, 3.69 mmol) was dissolved in 80 ml acetonitrile at 40° C. in an autoclavable bottle. $TiO_2$ nanoparticles (Degussa, P25, 1.00 g) were added into this solution. The mixture was sonicated for 10 min at room temperature (RT), and placed in an oven at 80° C. overnight. Sample was centrifuged at 4000 rpm, until clear solution was obtained. The excess stearic acid was washed three times by dispersing the solid into absolute ethanol using sonication for 5 min, followed by centrifugation. Pastry like product was dried in oven at 70° C. overnight. The powder cake was ground by agate mortar gently before use. Yield: 1.75 g.

Example 3: Method for Hydrophobicization of Nano Articles $TiO_2$, ZnO and $CeO_2$) Through Reaction with Silanes $TiO_2$, ZnO, or $CeO_2$ nanoparticles are reacted with a silane of formula $RSi(OR')_3$, $RSiX_3$, $R_2SiX_2$, or $R_3SiX$, where R is a hydrophobic group such as a hydrocarbon or fluorinated carbon chain including, but not limited to, methyl, octadecyl, stearyl, and perfluorooctadecyl groups.

The reaction of $TiO_2$ nanoparticles with perfluorooctanoyltriethoxysilane may occur as follows: $TiO_2$ nanopowder (Degussa, P25, 0.5 g) was placed in an autoclavable glass bottle with 10 mL of EtOH and sonicated for 45 minutes to fully disperse. 5 mL of EtOH was measured and adjusted to pH 11 by addition of aqueous $NH_3$ with stirring to ensure solution homogeneity. 0.15 mL of perfluorooctyltriethoxysilane was added to the basic EtOH and stirred rapidly at room temperature for 1 hour. Subsequently, this solution was poured into the $TiO_2$ dispersion and rapidly stirred at RT in the dark for approximately 22 hours.

The powder was centrifuged to collect and washed twice with EtOH. Yield: 0.51 g.

FIG. 1A shows a TEM image of perfluorooctytriethoxysilane treated $TiO_2$ particles. The small crystallites studding the larger crystals are siloxide crystallites.

Figure 1B:
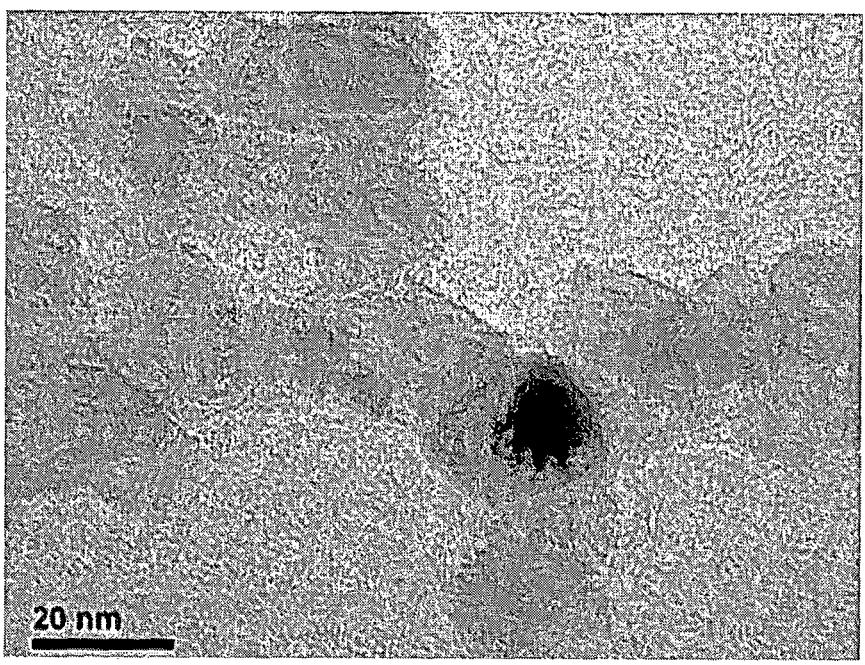
FIG. 1B shows a TEM image of 1H, 1H, 2H, 2H-perfluorooctyltriethoxysilane treated $TiO_2$ particles with PVP pre-treatment. A core-shell type structure is more prevalent in this case.

FIG. 1B shows a TEM image of perfluorooctyltriethoxysilane treated TiO2 particles with PVP pre-treatment. A core-shell type structure is more prevalent in this case.

Example 4: Method of Forming Liquid Marbles and Release Thereof

Hydrophobicized $TiO_2$ nanoparticles are placed in a petri-dish. A drop of water (10 µL) was gently rolled on the bed of hydrophobic particles until the droplet is encapsulated by hydrophobic particles. This droplet, which is a liquid marble, displays non-wetting properties and can be rolled on different hydrophilic surfaces such as glass and aluminum without wetting them. This is applicable to different hydrophobic particles, including but not limited to $TiO_2$, in all forms, both doped and undoped, as well as ZnO and $CeO_2$ as well as other metal, mixed metal oxides or mixtures thereof. Exposure to UV light and/or visible light converts the hydrophobic surfaces of the nanoparticles to hydrophilic surfaces, affording a photo-induced change in wettability of the nanoparticles.

Figure 4A:
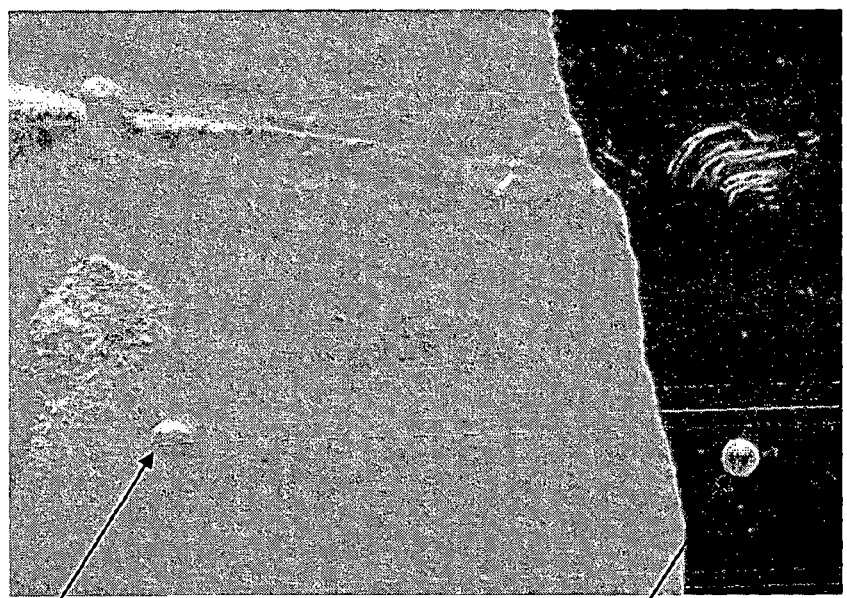
FIG. 4A shows a liquid marble containing an aqueous solution of Rhodamine B dye is resting on Al foil. The liquid marble appears pink. Another liquid marble containing the same solution of Rhodamine B dye is resting on a UV transilluminator and exposed to UV irradiation. This liquid marble appears yellow/orange due to the excited fluorescent Rhodamine B dye.

FIG. 4A shows a liquid marble containing an aqueous solution of Rhodamine B dye is resting on Al foil. The liquid marble appears pink. Another liquid marble containing the same solution of Rhodamine B dye is resting on a UV transilluminator and exposed to UV irradiation. This liquid marble appears yellow/orange due to the excited fluorescent Rhodamine B dye.

Figure 4B:
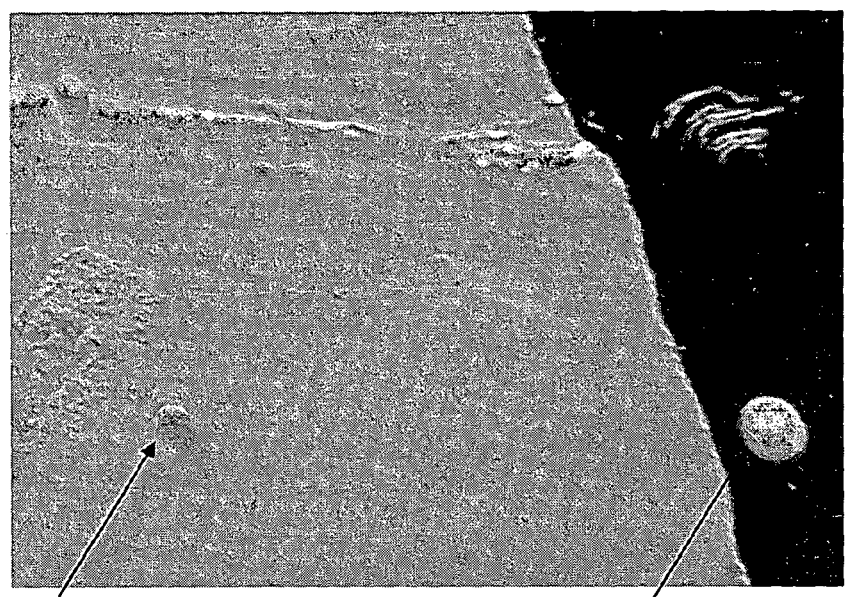
FIG. 4B shows the yellow/orange liquid marble of FIG. 4A exposed to UV light (303 nm, 4 minutes) collapses, leaving a yellow puddle.

FIG. 4B shows the yellow/orange liquid marble of FIG. 4A exposed to UV light (303 nm, 4 minutes) collapses, leaving a yellow puddle.

Figure 5A:
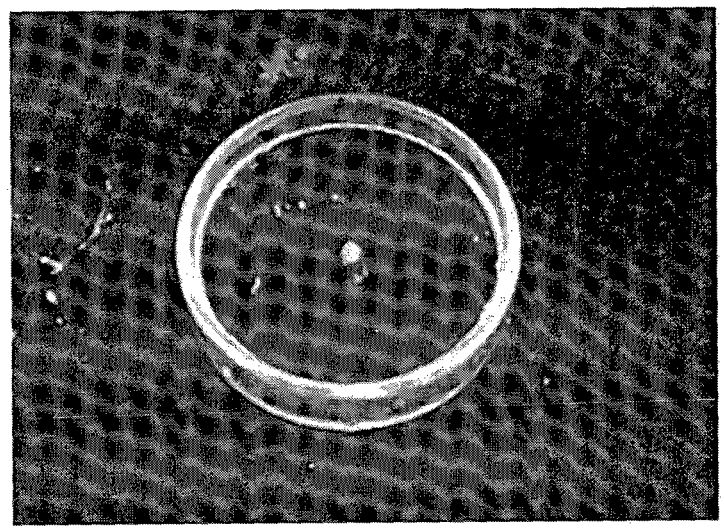
FIG. 5A shows a petri-dish with a pool of water. A liquid marble containing an aqueous solution of Rhodamine B dye is resting on the surface of the water pool.

FIG. 5A shows a petri-dish with a pool of water. A liquid marble containing an aqueous solution of Rhodamine B dye is resting on the surface of the water pool.

Figure 5B:
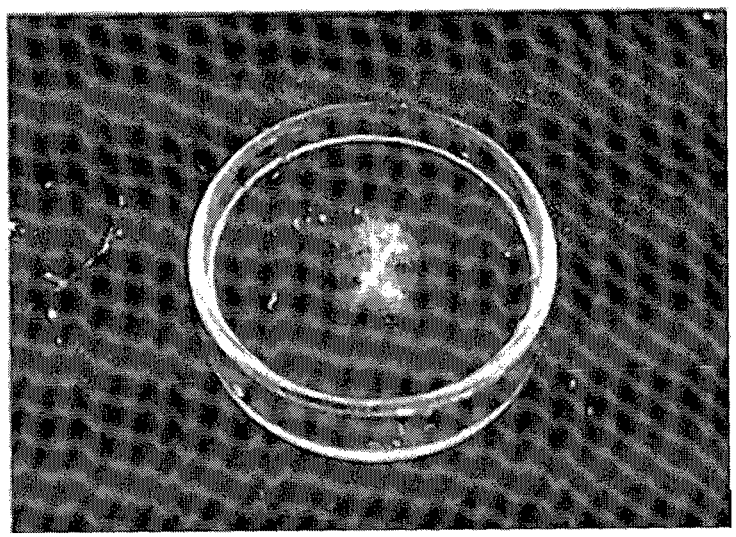
FIG. 5B shows that after irradiation with 303 nm light for 2 minutes, the liquid marble of FIG. 5A collapses and releases its contents into the bulk water.

FIG. 5B shows that after irradiation with 303 nm light for 2 minutes, the liquid marble of FIG. 5A collapses and releases its contents into the bulk water.

Example 5: $TiO_2$—Dry Water Formation and Release Thereof

Dry water may be formed as follows: Using $TiO_2$ nanoparticles coated with fluorinated silica affords dry water when mixed with water at a high shear rate. A homogenizer was used at a shear rate of 14,000 rpm for 2 minutes with 1.08 g of treated $TiO_2$ powder and 2.7 g of water, yielding a fluffy, free-flowing white powder. This powdery material is in essence micronized liquid marbles, also referred to as "dry water" or water-in-air microemulsions. The percentage weight of water is 71%.

Dry water may also be formed as follows: $TiO_2$ nanoparticles coated with fluorinated silica was weighed into a Teflon cup (0.7033 g). Water was added in approximately 0.2 mL quantities each time, followed by 30 seconds of homogenization at 14,000 rpm each time. A total of 3.0 mL of water was added. Due to some powder loss during homogenization, the percentage weight of water was obtained by measuring some dry water into a vial (0.3067 g of dry powder, empty vial weight=14.7180 g) and then drying it at 85° C. over 2 days, then subsequently measuring the weight of the dry powder and vial (14.7619 g, weight of dry powder=0.0439 g). The percentage weight of water obtained for dry water was approximately 86%.

Dry water may further be formed as follows: $TiO_2$ nanoparticles functionalized with stearic acid was placed in a Teflon cup (0.2546 g). 100 µL of DI water was added to the cup and homogenized at 6,000 rpm for approximately 10 seconds. A free-flowing powder was still obtained. An additional 50 µL of DI water was added to the cup and homogenized at 14,000 rpm for 10 seconds. Again, dry water was obtained as a free-flowing powder. Attempts to add more water for homogenization led to a paste instead. The percentage weight of water obtained was approximately 37%.

Figure 2:
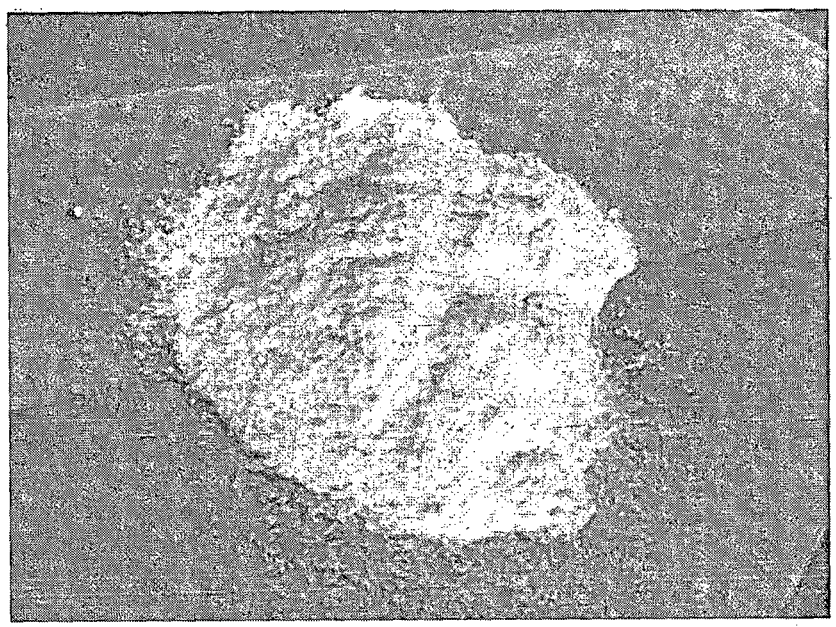
FIG. 2 shows a photograph of $TiO_2$-based dry water prepared by a method disclosed herein.

FIG. 2 shows a photograph of $TiO_2$-based dry water prepared by a method disclosed herein.

Figure 3A:
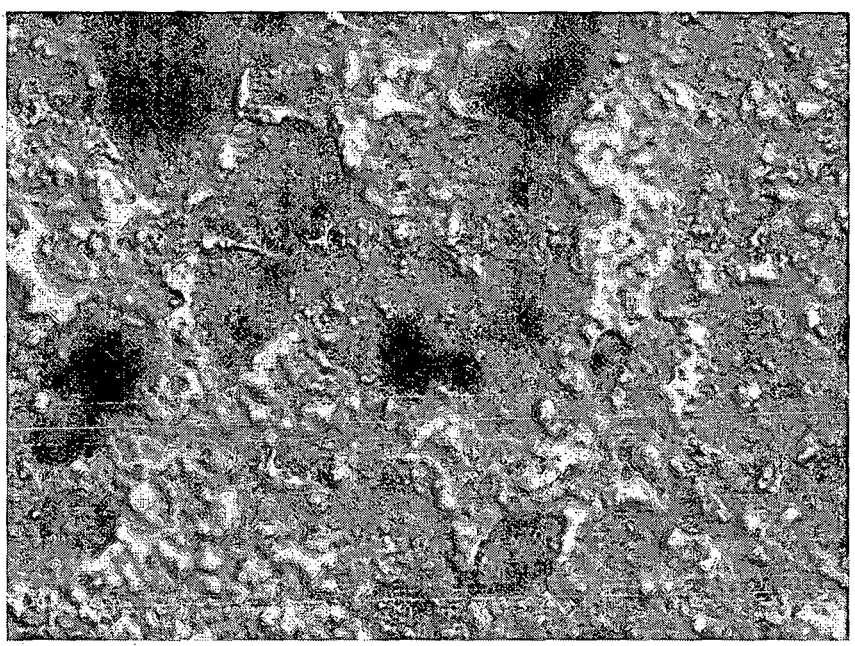
FIG. 3A shows an optical microscope image of $TiO_2$ dry water at 100× magnification after being left at room temperature for almost 5 days.

FIG. 3A shows an optical microscope image of $TiO_2$ dry water at 100× magnification after being left at room temperature for almost 5 days.

Figure 3B:
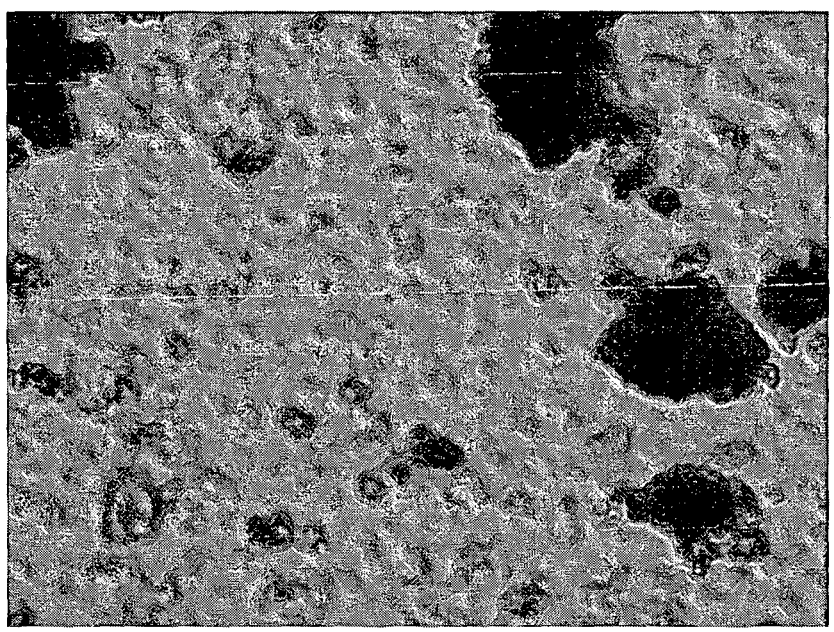
FIG. 3B shows an optical microscope image of $TiO_2/SiO_2$ starting material at 100× magnification. The globular structures in the dry water are translucent to light due to the presence of water in the micronized liquid marbles, whereas the large aggregates of the starting material appear dark and relatively opaque to light since the entire aggregate is composed of the $TiO_2/SiO_2$ particles.

FIG. 3B shows an optical microscope image of $TiO_2/SiO_2$ starting material at 100× magnification. The globular structures in the dry water are translucent to light due to the presence of water in the micronized liquid marbles, whereas the large aggregates of the starting material appear dark and relatively opaque to light since the entire aggregate is composed of the $TiO_2/SiO_2$ particles.

Water may be released from the dry water as follows: 0.4121 g of dry water was placed in a quartz tube. The tube was stoppered and placed in a Rayonet RPR-100 UV chamber and irradiated at 300 nm for three 5 minute intervals, with 1 minute in between each interval to check on the status of the dry water. With each irradiation session, the powder became less hydrophobic, and tended to stick to the walls of the quartz tube. After the $3^{rd}$ interval, water was observed to have been released from the dry water.

The powder was poured out into a vial and measured: 0.2638 g. The powder was placed in an oven at 85° C. overnight to remove the water. The remaining powder was weighed: 0.08813 g.

Not all the water was released after 15 minutes of irradiation. "Dry water" is far more stable to UV irradiation than liquid marbles. Therefore, this exercise shows that slow, photo-induced release can be achieved. Presumably longer periods of irradiation will induce further release of water from non-ruptured dry water.

FIG. 8 shows that the "dry liquid" has different release times under UV irradiation using a Rayonet Photoreactor Chamber.

Example 6: $TiO_2$—Dry Oil Formation and Release Thereof

Dry oil may be formed as follows: 0.3716 g of $TiO_2$/ fluorinated silica nanoparticles was added into a 20 mL vial. Vegetable oil (0.2779 g, Naturel Canola and Sunflower Oil) was slowly added and the mixture rapidly mixed with a spatula or a whisk until "dry oil" forms.

Dry oil may be released as follows: 0.6495 g of "dry oil" was scattered on a quartz dish. The sample was placed in a Rayonet RPR-100 UV chamber and irradiated at 300 nm for 7 minutes, after which oil was released, and the powder became a creamy substance.

Figure 6:
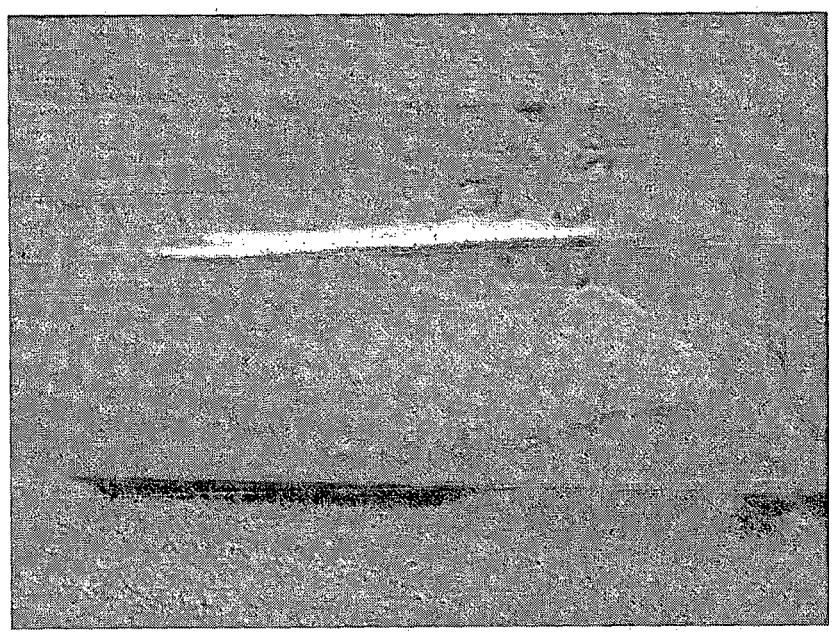
FIG. 6 shows a photograph of $TiO_2$-based "dry vegetable oil".

FIG. 6 shows a photograph of $TiO_2$-based "dry vegetable oil".

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

As used herein, the term "and/or" includes any and all combinations of one or more of the associated listed items.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. A method for releasing a substance from a macro- or micro-liquid marble, wherein the macro- or micro-liquid marble is formed by a plurality of nanoparticles and/or mixture of plurality of nanoparticles and said substance is encapsulated therein, the method comprising irradiating the plurality of nanoparticles at a wavelength of between about 200 nm and about 2,000 nm, wherein the plurality of nanoparticles is metal or metal oxide nanoparticles, and wherein the plurality of nanoparticles is grafted with oleophobic molecules comprising a fluorinated or a perfluorinated silane of formula $RSi(OR')_3$ or $RSiX_3$, wherein
R is a fluorinated or a perfluorinated $C_6$-$C_{18}$ alkyl; and
X is a halogen.

2. The method of claim 1, wherein R in $RSi(OR')3$ is CF3(CF2)5CH2CH2- or CF3(CF2)7CH2CH2-.

3. The method of claim 1, wherein the plurality of nanoparticles is comprised of titanium dioxide (TiO2), zinc oxide (ZnO), or cerium oxide (CeO2).

4. The method of claim 1, comprising irradiating the plurality of nanoparticles at a wavelength of between about 200 nm and about 2,000 nm with an intensity of more than 0.01 mW/cm2.

5. The method of claim 1, wherein the substance encapsulated by the macro- or micro-liquid marble is in liquid phase.

6. The method of claim 5, wherein the substance comprises water or an aqueous solution.

7. The method of claim 6, wherein the substance further comprises a pharmaceutical active ingredient, an anti-oxidant, a dispersant, a fertilizer, a pesticide, a herbicide, or a mixture thereof.

* * * * *

UNITED STATES PATENT AND TRADEMARK OFFICE
CERTIFICATE OF CORRECTION

PATENT NO. : 9,956,538 B2  
APPLICATION NO. : 14/764832  
DATED : May 1, 2018  
INVENTOR(S) : Jia Min Chin et al.

Page 1 of 1

It is certified that error appears in the above-identified patent and that said Letters Patent is hereby corrected as shown below:

On the Title Page

Item (30), Foreign Application Priority Data:  
Please replace foreign priority filing date "Feb. 15, 2015" with --Feb. 15, 2013--.

Signed and Sealed this  
Sixth Day of November, 2018

Andrei Iancu  
*Director of the United States Patent and Trademark Office*